(12) United States Patent
Edelman et al.

(10) Patent No.: US 10,219,792 B2
(45) Date of Patent: Mar. 5, 2019

(54) DEPLOYMENT SYSTEM INCORPORATING APPLICATION OF ADHESIVE

(71) Applicant: Boston Scientific Scimed, Inc., Maple Grove, MN (US)

(72) Inventors: Peter G. Edelman, Maple Grove, MN (US); Laura Elizabeth Christakis, Worcester, MA (US); Colby Harris, Weston, MA (US); Paul E. Zarembo, Vadnais Heights, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 328 days.

(21) Appl. No.: 14/720,105

(22) Filed: May 22, 2015

(65) Prior Publication Data

US 2015/0335321 A1 Nov. 26, 2015

Related U.S. Application Data

(60) Provisional application No. 62/002,286, filed on May 23, 2014.

(51) Int. Cl.

| | |
|---|---|
| *A61F 2/966* | (2013.01) |
| *A61B 17/00* | (2006.01) |
| *A61F 2/95* | (2013.01) |
| *A61F 2/24* | (2006.01) |
| *A61F 2/958* | (2013.01) |

(52) U.S. Cl.
CPC ...... *A61B 17/00491* (2013.01); *A61F 2/2427* (2013.01); *A61F 2/95* (2013.01); *A61F 2/966* (2013.01); *A61B 2017/003* (2013.01); *A61B 2017/00495* (2013.01); *A61B 2017/00522* (2013.01); *A61B 2017/00867* (2013.01); *A61F 2/2433* (2013.01); *A61F 2/2436* (2013.01); *A61F 2/958* (2013.01); *A61F 2220/005* (2013.01); *A61F 2220/0008* (2013.01)

(58) Field of Classification Search
CPC .... A61B 17/00491; A61B 2017/00495; A61B 2017/0052; A61F 2/2427; A61F 2/95; A61F 2/966
USPC ........................................... 623/1.36
See application file for complete search history.

(56) References Cited

U.S. PATENT DOCUMENTS

| | | | |
|---|---|---|---|
| 5,026,377 | A | 6/1991 | Burton et al. |
| 5,643,278 | A | 7/1997 | Wijay |
| 5,817,102 | A | 10/1998 | Johnson et al. |
| 5,993,460 | A | 11/1999 | Beitelia et al. |
| 6,136,006 | A | 10/2000 | Johnson et al. |
| 6,458,138 | B1 | 10/2002 | Sydney et al. |
| 6,572,645 | B2 | 6/2003 | Leonhardt |
| 6,645,240 | B2 | 11/2003 | Yee |
| 6,958,073 | B2 | 10/2005 | Rogers et al. |

(Continued)

FOREIGN PATENT DOCUMENTS

| | | |
|---|---|---|
| DE | 102004041259 A1 | 3/2006 |
| JP | 2005524487 | 8/2005 |

(Continued)

*Primary Examiner* — Katrina Stransky
(74) *Attorney, Agent, or Firm* — Seager, Tufte & Wickhem, LLP

(57) ABSTRACT

The present disclosure is directed to a delivery catheter with a mechanism of discharging an adhesive during and/or immediately prior to deployment of the medical device by the delivery catheter.

20 Claims, 9 Drawing Sheets

(56) References Cited

U.S. PATENT DOCUMENTS

| | | |
|---|---|---|
| 7,198,637 B2 | 4/2007 | Deshmukh et al. |
| 8,465,536 B2 | 6/2013 | Parker |
| 8,679,172 B2 | 3/2014 | Dorn et al. |
| 8,721,703 B2 | 5/2014 | Fowler |
| 8,747,448 B2 | 6/2014 | Argentine |
| 8,876,879 B2 | 11/2014 | Hartley et al. |
| 8,920,481 B2 | 12/2014 | Stiger |
| 2001/0014717 A1 | 8/2001 | Hossainy et al. |
| 2002/0029075 A1 | 3/2002 | Leonhardt |
| 2003/0120339 A1 | 6/2003 | Banik et al. |
| 2004/0199240 A1 | 10/2004 | Dorn |
| 2004/0210235 A1 | 10/2004 | Deshmukh et al. |
| 2004/0210299 A1 | 10/2004 | Rogers et al. |
| 2005/0065591 A1 | 3/2005 | Moberg et al. |
| 2006/0041302 A1 | 2/2006 | Malewicz |
| 2006/0282152 A1 | 12/2006 | Beyerlein et al. |
| 2007/0106364 A1 | 5/2007 | Buzzard et al. |
| 2007/0129785 A1 | 6/2007 | Vreeman et al. |
| 2007/0219612 A1* | 9/2007 | Andreas .......... A61B 17/12022 623/1.11 |
| 2007/0233227 A1* | 10/2007 | Greenan .................. A61F 2/07 623/1.13 |
| 2007/0270938 A1 | 11/2007 | Osypka |
| 2008/0234796 A1 | 9/2008 | Dorn |
| 2009/0088831 A1 | 4/2009 | Goto |
| 2010/0268328 A1 | 10/2010 | Stiger |
| 2011/0270371 A1 | 11/2011 | Argentine |
| 2011/0270372 A1 | 11/2011 | Argentine |
| 2011/0282195 A1* | 11/2011 | Solar ................. A61M 25/0026 600/431 |
| 2013/0178896 A1* | 7/2013 | Stenton ........... A61B 17/00491 606/213 |
| 2014/0135831 A1* | 5/2014 | White .............. A61B 17/00491 606/214 |
| 2014/0371844 A1* | 12/2014 | Dale .................... A61F 2/2418 623/2.11 |
| 2015/0045876 A1* | 2/2015 | Clerc ...................... A61F 2/82 623/1.38 |

FOREIGN PATENT DOCUMENTS

| | | |
|---|---|---|
| JP | 2008509711 | 4/2008 |
| JP | 2008529719 | 8/2008 |
| WO | 03094793 A1 | 11/2003 |
| WO | 2006014567 A2 | 2/2006 |
| WO | 2006088638 A1 | 8/2006 |
| WO | 2007109621 A2 | 9/2007 |
| WO | 2010083558 A1 | 7/2010 |

* cited by examiner

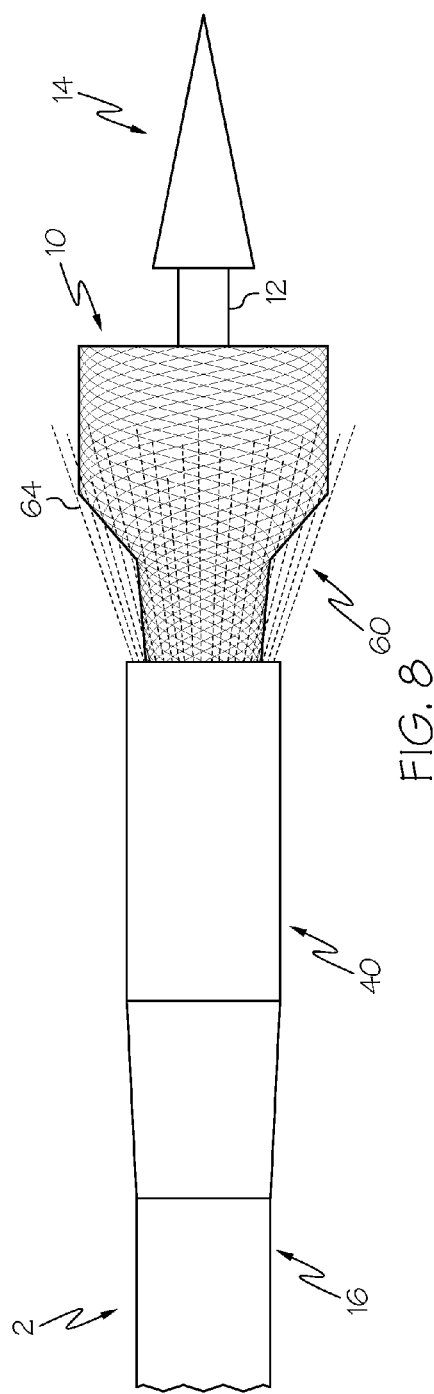
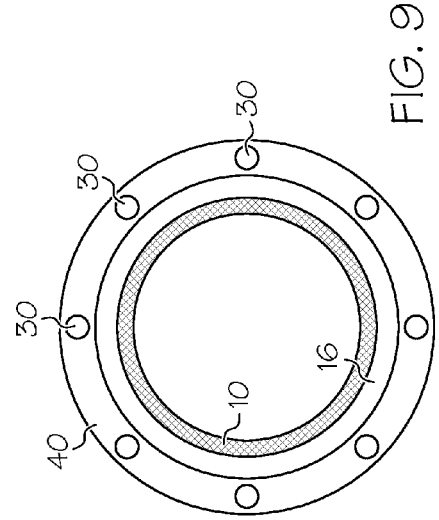

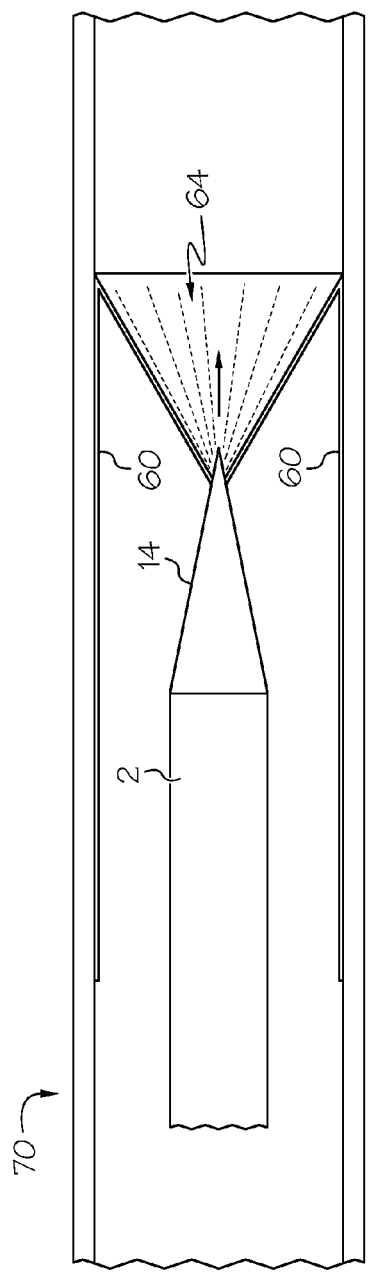
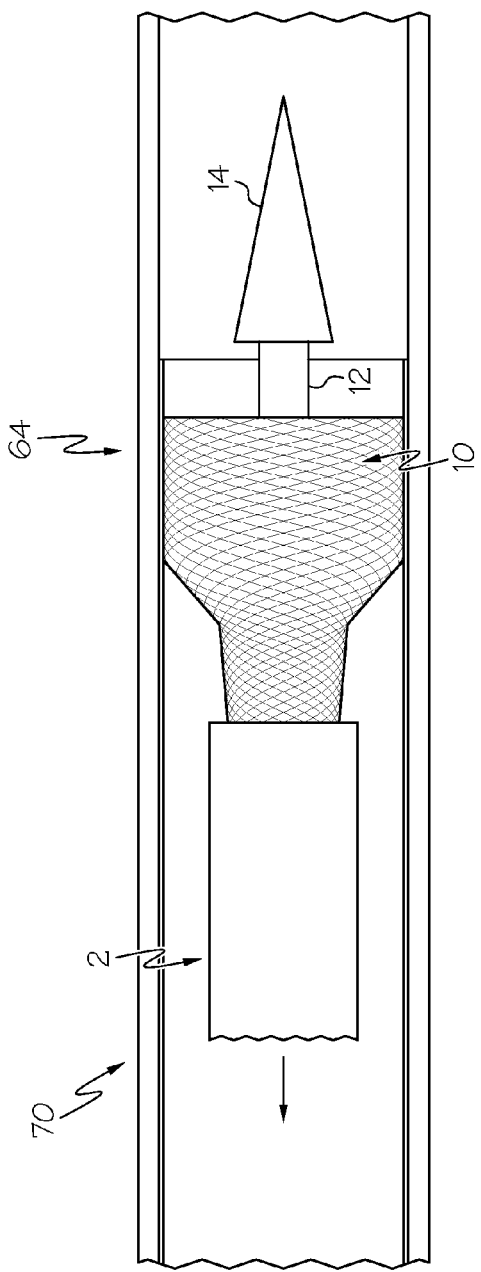
FIG. 10
FIG. 11

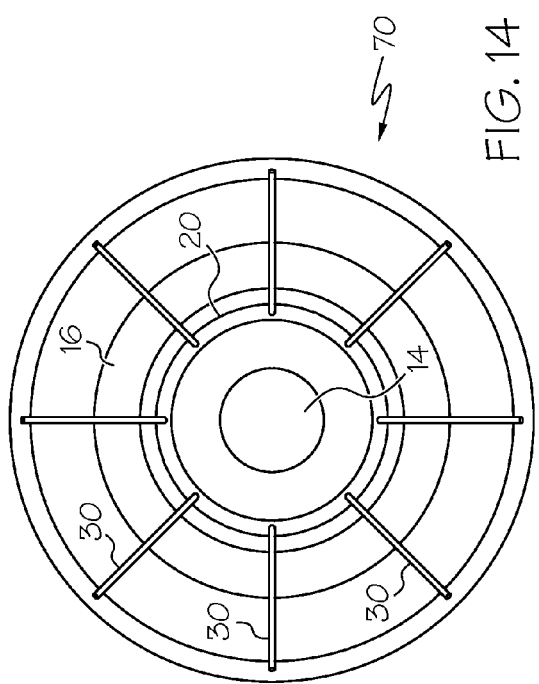
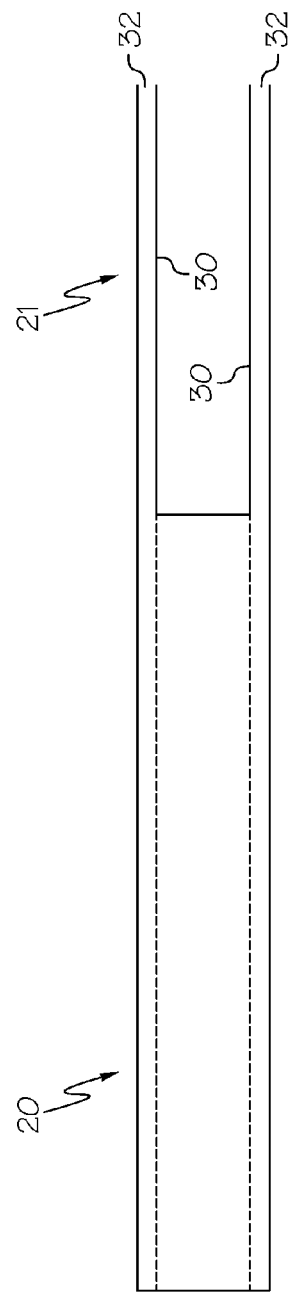

DEPLOYMENT SYSTEM INCORPORATING APPLICATION OF ADHESIVE

CROSS-REFERENCE TO RELATED APPLICATIONS

This Application claims the benefit of and priority to U.S. Provisional Application No. 62/002,286, filed May 23, 2014, the entire contents of which are herein incorporated by reference.

STATEMENT REGARDING FEDERALLY SPONSORED RESEARCH

Not Applicable

BACKGROUND

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Depending on the structure and conditions of a body lumen, stents can be prone to stent migration.

One way to reduce the risk of stent migration has been to expose bare metal portions of the stent to lumen tissue. The open, braided structure of the stent may provide a scaffold that promotes tissue ingrowth into the stent. This tissue ingrowth may aid anchoring the stent in place and may reduce the risk of migration. In some cases, however, tissue ingrowth has been known to lead to reocclusion of the body lumen. In addition, stents anchored by tissue ingrowth cannot be moved or removed without an invasive procedure. To reduce tissue ingrowth, stents have been covered with a coating (e.g., made of a polymer, etc.) to create a physical barrier between the lumen and the lumen wall. However, in some circumstance, such stents can have an unacceptable occurrence of migration, as compared to bare metal counterparts.

Another way to reduce the risk of stent migration has been to use a flared stent. However, stents having flares can have an unacceptable occurrence of migration.

All US patents and applications and all other published documents mentioned anywhere in this application are incorporated herein by reference in their entirety.

Without limiting the scope of the present disclosure a brief summary of some of the claimed embodiments is set forth below. Additional details of the summarized embodiments of the present disclosure and/or additional embodiments of the present disclosure may be found in the Detailed Description below.

SUMMARY

The present disclosure is directed to a delivery catheter with a mechanism for discharging an adhesive during and/or immediately prior to deployment of the medical device by the delivery catheter in order to reduce or prevent migration of the medical device after implantation.

In one aspect, a delivery catheter for a medical device comprises an inner shaft; an inner sheath extending around the inner shaft, the inner sheath comprising a distal end region; an adhesive delivery channel configured to deliver an adhesive, a distal end region of the adhesive delivery channel forming a part of the distal end region of the inner sheath, the adhesive delivery channel having a discharge opening; an outer sheath; characterized in that the distal end region of the adhesive delivery channel is configured to extend outward relative to the inner shaft upon an initial retraction of the outer sheath.

In a further aspect of the delivery catheter above where, in addition, the distal end region of the adhesive delivery channel is formed of a shape memory polymer or an electroactive polymer.

In a further aspect of the delivery catheter above where, in addition, the adhesive delivery channel is a plurality of adhesive delivery channels; the delivery catheter further comprises an extender forming a part of the distal end region of the inner sheath, each extender being positioned between two of the plurality of adhesive delivery channels forming the distal end region of the inner sheath, each extender configured to extend outward relative to the inner shaft upon the initial retraction of the outer sheath.

In a further aspect of the delivery catheter above where, in addition, the inner sheath comprises a protuberance; the outer sheath comprises a protuberance that is positioned distal to the protuberance of the inner sheath and configured to contact the protuberance of the inner sheath for concurrent retraction of the inner and outer sheaths.

In a further aspect of the delivery catheter above where, in addition, the discharge opening can be either a distal discharge opening or a side discharge opening.

In a further aspect of the delivery catheter above where, in addition, the delivery catheter further comprises a medical device positioned between the inner shaft and the inner sheath, the medical device positioned around the inner shaft, the distal end region of the inner sheath positioned around the medical device.

The medical device can be a self-expandable medical device. Alternatively, the medical device can be a balloon expandable medical device positioned on a balloon positioned on the inner shaft.

In a further aspect of the delivery catheter above where, in addition, the adhesive delivery channel is in fluid communication with an adhesive injection port located at a proximal end region of the delivery catheter.

In a further aspect of the delivery catheter above where, in addition, the adhesive delivery channel has two sub-channels to separately deliver parts of a two-part adhesive to a mixing mechanism positioned at the discharge opening of the adhesive delivery channel.

In a further aspect, a method of operating the delivery catheter above comprises: retracting the outer sheath for the initial retraction; and discharging an adhesive from the discharge opening of the adhesive delivery channel as the outer sheath is being further retracted from the initial retraction.

In a further aspect of the method of operating the delivery catheter above wherein the adhesive is a two part adhesive, the method further comprising mixing the two-part adhesive either prior to ejecting the two-part adhesive into the adhesive delivery channel or as the adhesive is being discharged from the adhesive delivery channel.

In a further aspect of the method of operating the delivery catheter above where the adhesive delivery channel having two sub-channels to separately deliver the two-part adhesive to a mixing mechanism positioned at the discharge opening of the adhesive delivery channel.

In a further aspect of the method of operating the delivery catheter above where discharging the adhesive comprises spraying the adhesive from the adhesive delivery channel.

In a further aspect of the method of operating the delivery catheter above further comprising expanding the balloon expandable medical device immediately after discharging the adhesive.

In another aspect a method of implanting a medical device in a body lumen comprises: advancing a delivery catheter carrying the medical device, the medical device being selected from the group consisting of stents and valves; discharging an adhesive from the delivery catheter during deployment of the medical device, the adhesive being discharged onto the medical device, a wall of the body lumen, or combinations thereof.

In a further aspect of the method of implanting a medical device above, the delivery catheter comprises an adhesive delivery channel having a discharge opening for discharging the adhesive.

In a further aspect of the method of implanting a medical device above, wherein the adhesive delivery channel is a plurality of adhesive delivery channels.

In a further aspect of the method of implanting a medical device above, wherein discharging the adhesive comprises depositing lines of the adhesive.

In a further aspect of the method of implanting a medical device above, where alternatively discharging the adhesive comprises spraying the adhesive.

In a further aspect of the method of implanting a medical device above, the adhesive delivery channel comprises a nozzle for spraying the adhesive.

In a further aspect of the method of implanting a medical device above, wherein the adhesive is discharged onto the medical device.

In a further aspect of the method of implanting a medical device above, wherein the adhesive is discharged onto the wall of the body lumen.

In a further aspect of the method of implanting a medical device above, wherein the delivery catheter comprises an adhesive injection port positioned at a proximal region of the delivery catheter, the adhesive injection port in fluid communication with the adhesive delivery channel. Alternatively n a further aspect of the method of implanting a medical device above, wherein the delivery catheter comprises a catheter adhesive reservoir in fluid communication with the adhesive delivery channel.

In a further aspect of the method of implanting a medical device above, wherein the delivery catheter comprising an outer sheath overlaying the medical device, the adhesive delivery channel secured to the outer sheath.

In a further aspect of the method of implanting a medical device above, wherein the delivery catheter comprises an outer sheath positioned over the medical device, the outer sheath defines the adhesive delivery channel; wherein retracting the outer sheath from the medical device and discharging the adhesive are concurrent.

In a further aspect of the method of implanting a medical device above, wherein the delivery catheter comprises: an inner sheath overlaying the medical device, the inner sheath comprising a distal end region and the plurality of adhesive delivery channels; an outer sheath having a distal end and positioned over the inner sheath so that the distal end of the outer sheath is distal to the distal end region of the inner sheath; wherein upon retraction of the outer sheath relative to the inner sheath, the plurality of adhesive delivery channels extend outward for discharging adhesive onto the wall of the body lumen during deployment of the medical device.

In a further aspect of the method of implanting a medical device above, wherein a circumference of the distal end region of the inner sheath is discontinuous.

In a further aspect of the method of implanting a medical device above, wherein the plurality of adhesive delivery channels comprise a shape memory polymer or an electroactive polymer.

In another aspect, a delivery catheter for a medical device comprises: an inner shaft; an inner sheath extending around the inner shaft, the sheath comprising a distal end region and an adhesive delivery channel comprising a discharge opening, the adhesive delivery channel forming the distal end region of the inner sheath; and an outer sheath; wherein the distal end region of the inner sheath is configured to extend outward relative to the inner shaft upon an initial retraction of the outer sheath.

In yet another aspect, a method of implanting a medical device in a body lumen comprises: advancing a delivery catheter carrying the medical device, the delivery catheter comprising a distal tip; discharging an adhesive from the distal tip of the delivery catheter onto an inner surface of the body lumen; and deploying the medical device in the body lumen immediately after discharging the adhesive.

In a further aspect of the method of implanting a medical device above, the delivery catheter further comprises an adhesive delivery channel having a discharge opening, the adhesive delivery channel positioned in the distal tip of the delivery catheter.

In a further aspect of the method of implanting a medical device above, the delivery catheter further comprises an inner shaft secured to the distal tip, the adhesive delivery channel further positioned in a wall of the inner shaft.

In a further aspect of the method of implanting a medical device above, wherein the delivery catheter is moved in a first direction while discharging the adhesive and the delivery catheter is moved in a second direction opposite the first direction while deploying the medical device.

These and other embodiments are pointed out with particularity in the claims annexed hereto and forming a part hereof However, for further understanding reference can be made to the drawings which form a further part hereof and the accompanying descriptive matter, in which one or more embodiments are illustrated and described.

BRIEF DESCRIPTION OF THE SEVERAL VIEWS OF THE DRAWING(S)

FIG. 8 is a simplified view of adhesive being sprayed onto a medical device.

FIG. 9 is a simplified cross-sectional view of the delivery catheter of FIG. 8 (inner shaft and distal tip omitted for simplicity).

FIGS. 10-11 are simplified views of the distal end region of a delivery catheter in a body lumen, spraying adhesive onto the lumen wall prior to deployment of the medical device.

FIG. 14 is a simplified end view of the catheter of FIG. 13 showing the adhesive delivery channels extending radially outward.

FIG. 15 is a simplified side view of a portion of the inner sheath of the delivery catheter of FIG. 12.

DETAILED DESCRIPTION

Figure 1:
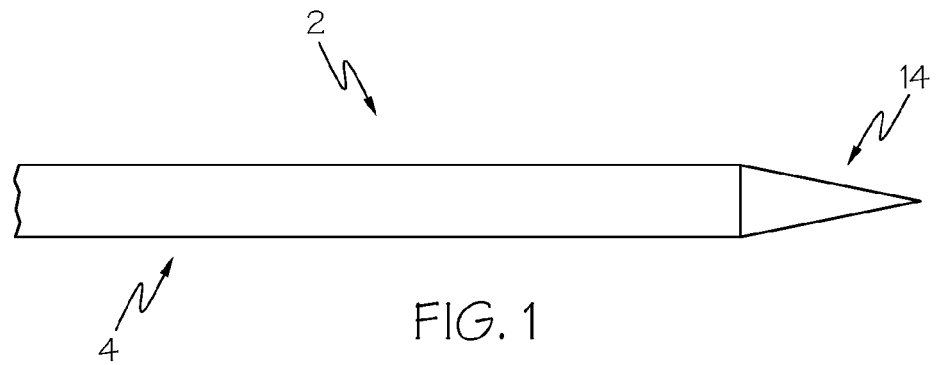
FIG. 1 is a simplified partial side view of the distal end region of a delivery catheter.

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

As used in this disclosure, "proximal" refers to a direction toward the operator of the catheter, and "distal" as used herein refers to a direction away from an operator of the catheter of the present disclosure.

As used in this application, an "end" is the last or endmost part of an element, and an "end region" is the portion adjacent to the end.

As used in this disclosure, a "region" is a section of the tubular medical device that extends from a first longitudinal position to a second longitudinal position and extends around the entire circumference of the tubular medical device.

As used in this disclosure, a "diameter" is the distance of a straight line between two opposite points and passing through the center of the element, for example, the adhesive delivery channel.

As used in this disclosure, an "adhesive delivery channel" is a tubular passage configured to deliver an adhesive.

As used in this disclosure, a "delivery catheter" is a catheter configured to delivery either a self-expandable medical device or a balloon expandable medical device.

As used in this disclosure, a "loaded delivery catheter" has a medical device positioned on the catheter for delivery to a body lumen.

As used in this disclosure, "deployment" refers to the expansion of the medical device from a delivery state to an implanted state in a body lumen.

The present disclosure is directed to a delivery catheter with a mechanism for discharging an adhesive during and/or immediately prior to deployment of the medical device by the delivery catheter (e.g. FIGS. 1-14). Thus, a single device is used to deliver the adhesive and to deliver/deploy the medical device.

For a self-expandable medical device the adhesive can be applied during and/or immediately prior to deployment, while for a balloon expandable medical device, the adhesive is applied immediately prior to deployment. The adhesive can be applied directly to the medical device 10 (e.g. FIGS. 6-8, 13), directly to the lumen wall 70 (e.g. FIGS. 10-11), or directly to both the medical device and to the lumen wall (not shown). For a balloon expandable medical device, adhesive discharged onto the lumen wall minimizes the amount of adhesive that may be deposited onto the balloon. The adhesive can be in liquid flowable form or encapsulated (e.g. in microcapsule form). Administration of an adhesive reduces or prevents migration of a medical device after implantation.

Adhesives suitable for the present disclosure include, but are not limited to: reactive polyfunctional oligomers that react quickly but slowly enough to allow delivery without solidifying in the delivery device (discussed below in greater detail); biocompatible polymer dissolved in a water miscible solvent (discussed below in greater detail); free radical redox system (discussed below in greater detail); an injectable fixation polymer that solidifies with a change in either pH or temperature (e.g. a stimuli responsive polymer/smart polymer); liquid adhesives (e.g. LifeSeal GI™ produced by LifeBond; DERMABOND ADVANCED® distributed by Ethicon, Inc. a Johnson & Johnson company); solutions of poloxamers and bioadhesive polymers that transition into a gel state at body temperature (discussed for example at Han-Gon Choi, Yu-Kyoung Oh, Chong-Kook Kim, *In situ gelling and mucoadhesive liquid suppository containing acetaminophen: enhanced bioavailability*, International Journal of Pharmaceutics, Vol. 165, Issue 1, pages 23-32, 20 Apr. 1998; hereby incorporated by reference in its entirety); adhesives in microcapsular form (discussed below in greater detail); tissue-adhesive functional groups (discussed below in greater detail); tissue adhesive coating (discussed in greater detail in commonly owned U.S. Patent Application No. 2012/0245663, hereby incorporated in its entirety); synthetic materials with tissue adhesive properties (alone or admixed with a carrier material, as discussed in greater detail in commonly owned U.S. Patent Application No. 2012/0245663); naturally derived materials with tissue adhesive properties (alone or admixed with a carrier material, as discussed in greater detail in commonly owned U.S. Patent Application No. 2012/0245663); and combinations thereof.

Figure 6:
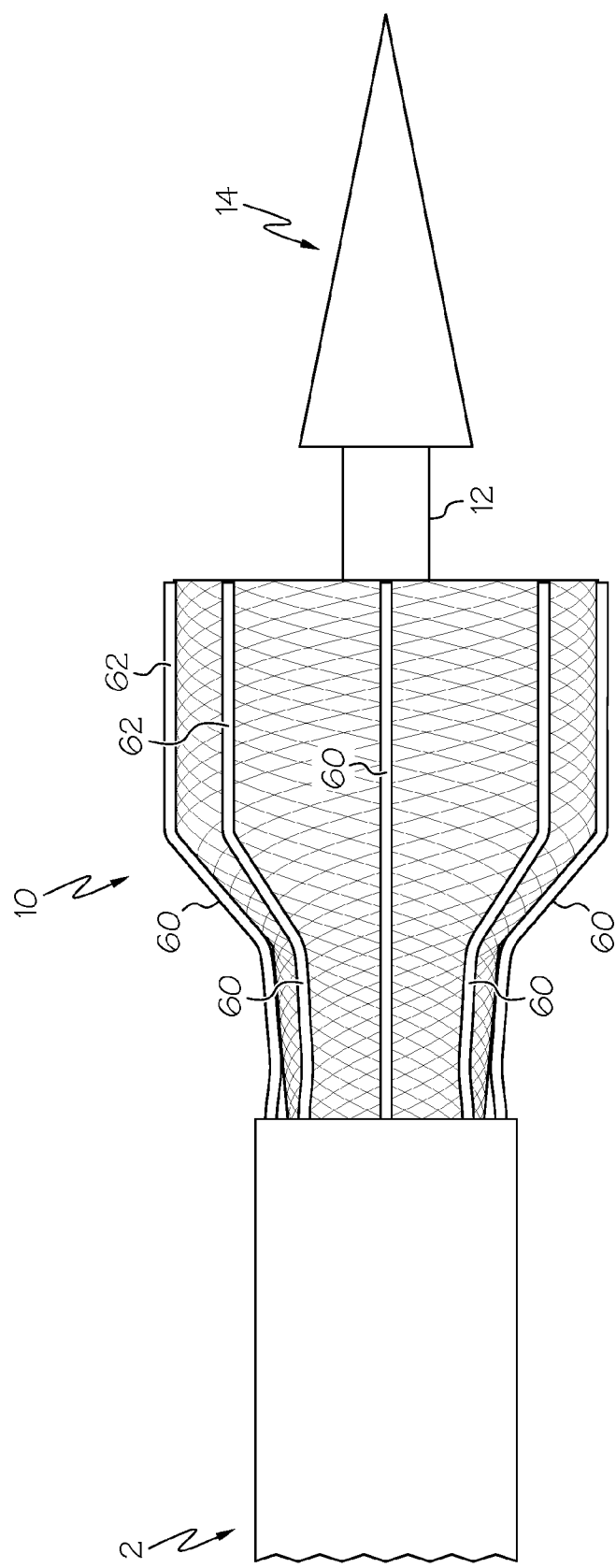
FIG. 6 is a simplified view of adhesive being applied in longitudinal lines onto a medical device during implantation of the medical device.
Figure 7:
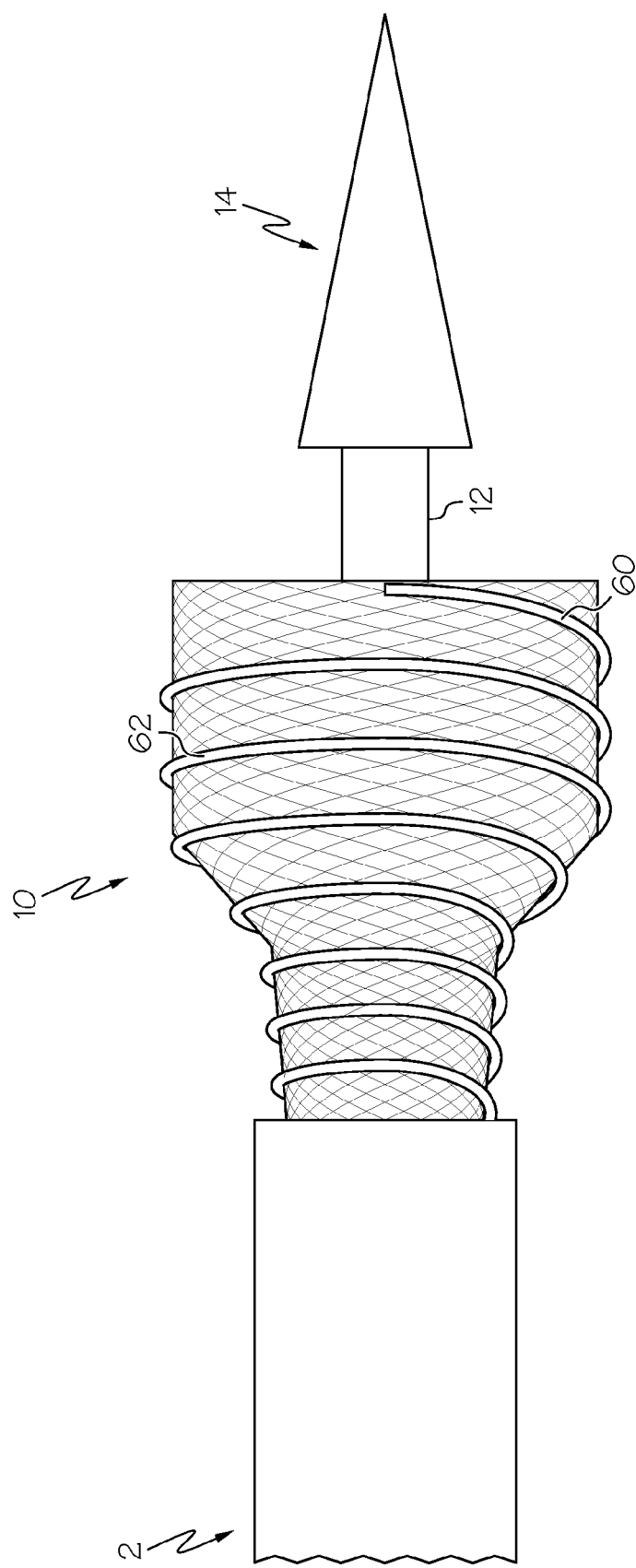
FIG. 7 is a simplified view of adhesive being applied in a helical line onto a medical device during implantation of the medical device.
Figure 12:
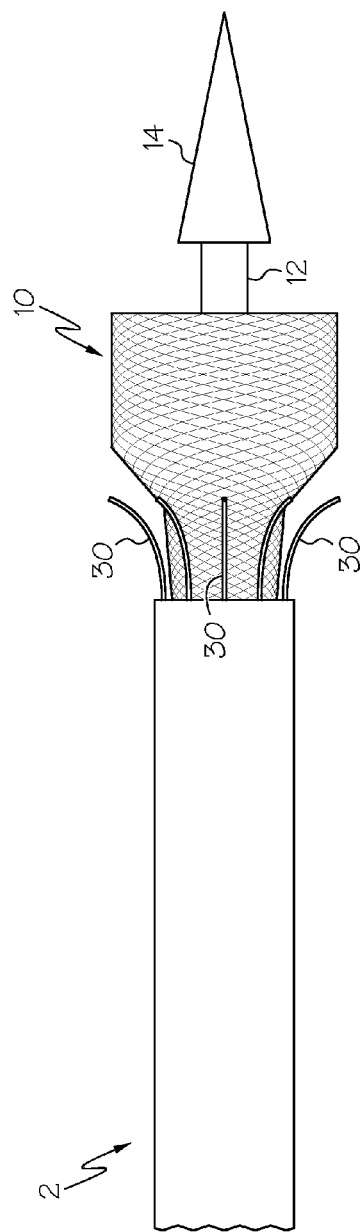
FIG. 12 is a simplified view of the distal end region of a delivery catheter of FIG. 1 with adhesive delivery channels forming a distal end region of the inner sheath.
Figure 13:
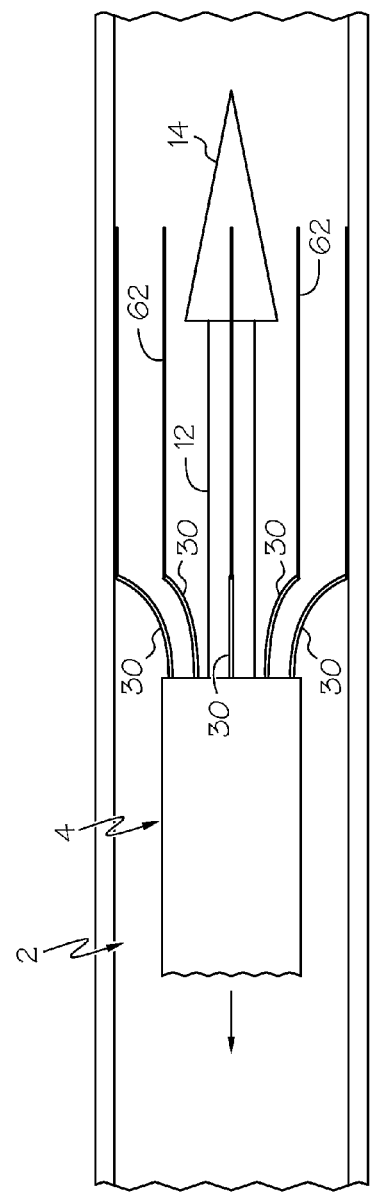
FIG. 13 is a simplified view of the delivery catheter of FIG. 12 showing application of adhesive onto a lumen wall by the adhesive delivery channels of the inner sheath (the medical device is omitted for simplicity).

The adhesive 60 can be applied in at least one line 62 (e.g. FIG. 6 (longitudinal), FIG. 7 (helical), and FIG. 9), or sprayed 64 (e.g. FIGS. 8 and 10). The adhesive can be continuously or discontinuously applied. Therefore, to modify the adhesive coverage area (the area upon which adhesive is to be deposited), the number of adhesive delivery channels can be modified; the adhesive delivery channels can be configured to spray the adhesive; and combinations thereof.

In one aspect, the adhesive covers an entirety of the outer surface of the medical device 10 (i.e. all regions of the medical device), or an entirety of a longitudinal segment of lumen wall 70 during implantation of the medical device 10 (e.g. FIGS. 11-14). In another aspect, the adhesive covers only a portion of the outer surface of the medical device (i.e. selected regions of the medical device), or only a portion of a longitudinal segment of lumen wall 70 (e.g. FIGS. 1-10). In one aspect, adhesive is not applied to a proximal end region of the medical device. Without being bound by theory, if adhesive is not applied to the proximal end region of the medical device, the proximal end region of the medical device would be easier to manipulate if the medical device needed to be moved within, or removed from, the body lumen.

The medical device 10 can be implanted in the gastrointestinal system, including, but not limited to, esophagus, biliary tract, and colon; the trachea; the cardiovascular system; the urinary tract; and elsewhere in the body (e.g., any lumen of the body). The medical device can be a tubular medical device such as a stent or a valve. The tubular medical device can include a covering (liner or graft) on an inner surface, an outer surface or both the inner and outer surfaces, to prevent tissue ingrowth as is known in the art.

In addition to the adhesive delivery system, the delivery catheter 2 can include one or more of the following elements: an outer shaft/sheath 16; an inner sheath 20; an inner shaft 12; a distal tip 14; an external element 40; and/or a balloon. Additional structures or features than those specifically discussed in this disclosure may also be included in the delivery catheter 2. The sheaths 16, 20 and shaft 12 can be tubular and define a lumen.

Adhesive Delivery System/Mechanism for Discharging an Adhesive

The mechanism for discharging an adhesive includes at least one adhesive delivery channel 30 (e.g. FIGS. 1-14). This can also be considered as an adhesive delivery system.

In one embodiment, the delivery catheter 2 has one adhesive delivery channel 30 (a single adhesive delivery channel). In another embodiment, the delivery catheter 2 has a plurality of adhesive delivery channels 30 (e.g. FIGS. 2, 3, 9, and 14). For example, the delivery catheter 2 can have two, three, four, five, six, seven, eight, or more adhesive delivery channels 30. In some embodiments, the adhesive delivery channels are uniformly spaced about the circumference (e.g. FIGS. 2, 3, 9, and 14). In some embodiments, the adhesive delivery channels 30 have a circular cross-section, while in other embodiments the adhesive delivery channels 30 have a rectangular cross-section. Other cross-sectional shapes are also suitable.

As discussed below in greater detail, the adhesive delivery channels 30 can be positioned external to the outer sheath (e.g. FIGS. 8-9); can be positioned in the wall of the outer sheath (e.g. FIGS. 2-3); can be positioned in the wall of the inner sheath (e.g. FIGS. 13-15); can be positioned in the wall of the inner shaft 12 (e.g. FIGS. 10-11); can be positioned in the distal tip 14 (e.g. FIGS. 10-11); and combinations thereof.

In some embodiments, the adhesive delivery channels 30 have a diameter less than the wall thickness of the sheath 16, 20 (e.g. FIGS. 2-3), the external element 40 (e.g. FIG. 9), or a thickness of the distal tip 14.

The adhesive delivery channel diameter is as large as possible without negatively impacting the structural strength of the sheath 16, 20 or the external element 40. For example, where the wall thickness of the sheath is 200 μm, the adhesive delivery channel diameter may preferably be in the range of 100 μm, assuming it is positioned symmetrically in the thickness of the wall. But this also depends on the number of adhesive delivery channels. The higher the number of adhesive delivery channels, the less the diameter needs to be. So for example where there are eight adhesive delivery channels 30, and the wall thickness of the sheath 16, 20 or external element 40 is 200 μm, each adhesive delivery channel diameter might preferably be 50 μm.

In designing the adhesive delivery channel, consideration needs to be given to the rheological properties of the adhesive, as well as the cure speed which will increase the viscosity as a function of time. In the case of a low viscosity adhesive, the adhesive delivery channel diameter can be smaller. But in the case of a higher viscosity adhesive, the adhesive delivery channel diameter needs to be larger so as to reduce the amount of injection pressure needed to apply the adhesive. In the case of a two part adhesive system that reacts on mixing, the adhesive delivery channel diameter must be large enough to allow for the increase in viscosity that will occur as the reaction ensues.

In designing the adhesive delivery channel, consideration also needs to be given to the mechanical properties of the delivery system catheter. The sheath 16, 20 and the external element can be formed by any suitable material. Some exemplary materials include poly (ether esters) (e.g. Hytrel®); poly(ether amides) (e.g. Pebax®); nylons; polyurethanes; polyethylene, and combinations thereof. In the case of a lower modulus material, such as Pebax® 6333, the adhesive delivery channel 30 would need to be a smaller to minimize any ballooning of the adhesive delivery channels 30 during delivery due to the increase in pressure. The design also needs to be such that the risk of wall rupture is minimized Conversely for a higher modulus material such as Pebax® 7233, the adhesive delivery channel 30 diameter can be a larger fraction of the wall thickness of the sheath 16, 20 or external element 40.

Figure 2:
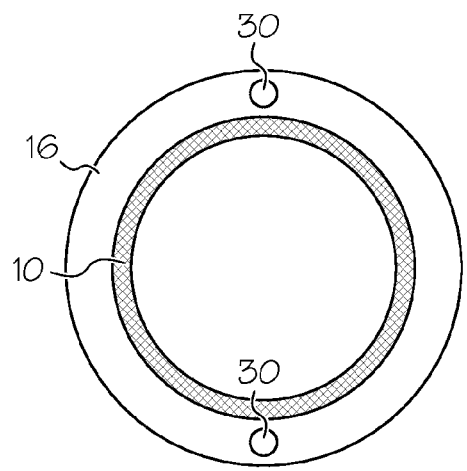
FIG. 2 is a simplified cross-sectional view of the delivery catheter of FIG. 1 (inner shaft and distal tip omitted for simplicity).
Figure 3:
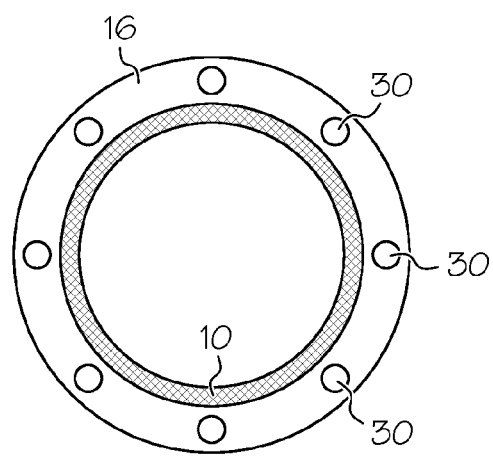
FIG. 3 is a simplified cross-sectional view of the delivery catheter of FIG. 1 (inner shaft and distal tip omitted for simplicity).

Each adhesive delivery channel 30 has at least one discharge opening 32 for discharging adhesive from the adhesive delivery channel (e.g. FIGS. 2-3 and 9). In one embodiment, each adhesive delivery channel 30 has one discharge opening (a single discharge opening). In another embodiment, each adhesive delivery channel 30 has a plurality of discharge openings. As discussed below in greater detail, the discharge opening 32 can be a distal discharge opening or a side discharge opening.

A discharge opening 32 at the distal end of the adhesive delivery channel 30 is a distal discharge opening (e.g. FIGS. 2-3 and 9). In other words, the distal discharge opening is the end opening of the adhesive delivery channel. The discharge opening 32 can face distally (e.g. FIG. 2), or can face outward relative to the longitudinal axis of the catheter (e.g. FIG. 10). In one embodiment, the adhesive delivery channel 30 has a single distal discharge opening. As discussed below in greater detail, distal discharge openings can discharge adhesive onto a medical device 10 or a lumen wall 70.

A discharge opening that extends through the wall of the adhesive delivery channel is a side discharge opening (not shown). The side discharge opening can either be directed outwards or inwards relative to the longitudinal axis of the catheter, as discussed below in greater detail. In one embodiment, the adhesive delivery channel 30 has a single side discharge opening and no distal discharge opening (distal end is sealed). In another embodiment, the adhesive delivery channel 30 has a side discharge opening and a distal discharge opening. As discussed below in greater detail, side discharge openings can discharge adhesive onto a medical device or a lumen wall 70.

In at least one embodiment, some adhesive delivery channels have a distal discharge opening and other adhesive delivery channels have a side discharge opening.

As discussed above, in a further aspect, the discharge opening 32 is configured to spray the adhesive from the adhesive delivery channel. Adhesive can be sprayed from the discharge opening by a nozzle or by an adhesive injector (not shown). In one aspect, the nozzle is a reduced diameter portion of the adhesive delivery channel. The reduced diameter portion can include the discharge opening, or be positioned proximal to the discharge opening. In one aspect, the adhesive delivery channel distal to the reduced diameter portion is flared outward to that the discharge opening has a greater diameter than the reduced diameter portion. Where an adhesive injector is utilized, the spray coating parameters may be controlled by a program of an external piece of equipment that is in communication with the adhesive injector (not shown).

Adhesive Delivery Channels External to the Outer Sheath

As discussed above, the adhesive delivery channels 30 can be positioned externally to the outer sheath 20. The distal end of adhesive delivery channels positioned externally to the outer sheath and the distal end of the outer sheath are coextensive.

In some embodiments, the adhesive delivery channels are tubes secured to an outer surface of the outer sheath that extend to, and coextensive with, the distal end of the outer sheath (not shown). In one embodiment, the longitudinal axis of the adhesive delivery channel is parallel to the longitudinal axis of the outer sheath. In other words, the adhesive delivery channel is non-coaxial to the outer sheath. Thus, these adhesive delivery channels can be described as a non-coaxial external element.

In other embodiments, the adhesive delivery channels 30 can be positioned in the wall of an external element 40 secured to the outer sheath 20 (e.g. FIGS. 8-9). Although the external element 40 is coaxial with the outer sheath 20 (a coaxial external element), the adhesive delivery channels are not coaxial with the outer sheath. In one embodiment, the adhesive delivery channels are positioned between an inner surface and an outer surface of the external element 40. The external element 40 can extend to the adhesive injection port, or can have a length that is less than the outer sheath (e.g. the external element defines a catheter adhesive reservoir).

Adhesive delivery channels with side discharge openings directed radially outwards can discharge adhesive onto a lumen wall 70. Adhesive delivery channels with distal discharge openings can discharge adhesive onto a medical device (e.g. FIG. 6-8) and/or onto a lumen wall 70 (e.g. FIG. 10). The adhesive delivery channels can have a distal discharge opening (e.g. FIG. 8), side discharge openings directed radially outwards (not shown), or a distal discharge opening and a side discharge opening. In at least one embodiment, some adhesive delivery channels have a distal discharge opening, and other adhesive delivery channels have a side discharge opening. In this embodiment, the outer element 40 can discharge adhesive onto the outer surface of the medical device through the distal discharge openings and onto the lumen wall through the side discharge openings.

Because these adhesive delivery channels secured to the outer sheath, they are retracted with the retraction of the outer sheath 20 and adhesive is discharged from the adhesive delivery channels as the outer sheath is retracted (helical and/or longitudinal retraction of the outer sheath with or without an inner sheath is discussed above). For adhesive delivery channels external to the outer sheath, the adhesive is discharged during deployment of a self-expandable medical device and immediately prior to deployment of a balloon expandable medical device.

Adhesive Delivery Channels Defined by Outer Sheath

As discussed above, the adhesive delivery channels 30 can be positioned in the wall of the outer sheath 16 (e.g. FIGS. 2-3). In one embodiment, the adhesive delivery channels are positioned between an inner surface and an outer surface of the outer sheath.

Side discharge openings directed radially outwards discharge adhesive onto a lumen wall. Side discharge openings directed radially inwards discharge adhesive onto the outer surface of a medical device. Distal discharge openings discharge adhesive onto a medical device (e.g. FIG. 6-7) and/or onto a lumen wall. The adhesive delivery channels can have a distal discharge opening (e.g. FIGS. 2-3), side discharge openings directed radially outwards (not shown), or a distal discharge opening and a side discharge opening. In at least one embodiment, some adhesive delivery channels have a distal discharge opening and other adhesive delivery channels have a side discharge opening. In this embodiment, the adhesive delivery channels 30 can discharge adhesive onto the outer surface of the medical device through the distal discharge openings or side discharge openings directed radially inward, and onto the lumen wall through the side discharge openings directed radially outward.

Adhesive is discharged from the adhesive delivery channels 30 as the outer sheath 16 is retracted (retraction of the outer sheath with or without an inner sheath is discussed above). For adhesive delivery channels external to the outer sheath, the adhesive is discharged during deployment of a self-expandable medical device and immediately prior to deployment of a balloon expandable medical device.

Adhesive Delivery Channels Defined by Inner Sheath

As discussed above, the adhesive delivery channels 30 can be positioned in the wall of the inner sheath 20 (e.g. FIGS. 12-15). In one embodiment, the adhesive delivery channels are positioned between an inner surface and an outer surface of the inner sheath.

In at least one embodiment, the adhesive delivery channels 30 form a distal end region 21 of the inner sheath 20. In some embodiments, the distal end region 21 is formed only by the adhesive delivery channels 30 separated by slits (open space). In other embodiments, the distal end region 21 is formed by adhesive delivery channels 30 and extenders (not shown). The extenders can be positioned in areas where no adhesive is to be discharged from the delivery catheter. For example, if the number of adhesive delivery channels is such that the slits are large, as shown for example by the inner sheath in FIG. 15 that has two adhesive delivery channels forming the distal end region 21, extenders can be included between the adhesive delivery channels to minimize the size of the slits. Thus, between two adhesive delivery channels, there can be no extenders, one extender, or a plurality of extenders. The extenders can be solid or tubular and are not in fluid communication with either an adhesive delivery port or with an adhesive reservoir. Although, no adhesive is discharged from an extender, the extender mimics the movement/positions of the adhesive delivery channels as discussed below in greater detail.

When the distal end region 21 of the inner sheath 20 is positioned inside the lumen of the outer sheath 16, the distal end region 21 is tubular with the adhesive delivery channels 30 being longitudinally oriented (e.g. FIG. 15). In some embodiments, the distal end region 21 of the inner sheath 20 extends outward after retraction of the outer sheath 16. In other words, a distal end region 21 of the adhesive delivery channel(s) and extenders if present, extends outward after retraction of the outer sheath 16 off the distal end region 21. In one embodiment, the slits become wider as the adhesive delivery channels 30, and extenders if present, extend outwards. When extended outwards, the adhesive delivery channels 30, and extenders if present, are either straight, curled, or have at least one bend. In one aspect, the distal end region 21 self-expands or biased to expand outwards and assume a position where there is no internal stress or strain. Some examples of materials that can be configured to expand or be biased outward include shape memory materials (metallic or polymeric), and electroactive polymers. In another aspect, the distal end region 21 expands outward due to radial expansion of the medical device.

In addition, the inner sheath includes a protuberance that contacts a respective protuberance protruding from the inner surface of the wall of the outer sheath (not shown). When the distal end region of the adhesive delivery channel expands outward after partial retraction of the outer sheath, the protuberance of the outer sheath contacts the protuberance of the inner sheath so that further retraction of the outer sheath also retracts the adhesive delivery channels of the inner sheath with adhesive being delivered concurrently with the retraction of the adhesive delivery channels. Thus, the protuberance of the inner sheath is positioned proximal to the protuberance of the outer sheath. The protuberances can be in the form of annular rings.

In some embodiments, the adhesive delivery channels 30 have distal discharge openings. In this embodiment, when the adhesive delivery channels 30 extend outwards, the distal discharge openings are directed toward the lumen wall so that adhesive is deposited from the adhesive delivery channels 30 onto the lumen wall.

In some embodiments, the distal ends of the adhesive delivery channels 30 of the inner sheath 20 are positioned distal to the distal end of a medical device 10 compressed in the delivery catheter. In one embodiment, the outer sheath 16 is retracted from the distal end region 21 of the inner sheath 20 so that the adhesive delivery channels 30 extend outwards to discharge adhesive onto the lumen wall, and thereafter, the outer and inner sheaths 16, 20 are withdrawn simultaneously to deploy the medical device and to continue discharging adhesive.

In other embodiments, the adhesive delivery channels 30 have a closed distal end and a side discharge opening. In some embodiments the side discharge opening is directed inwards towards the outer surface of the medical device. In one embodiment, the side discharge opening is adjacent the distal end of the medical device positioned in the delivery device. In this embodiment, adhesive is discharged through the side opening of the adhesive delivery channel and onto the outer surface of the medical device as the medical device is being deployed.

In another embodiment, the side opening is directed outward towards the lumen wall. In this embodiment, adhesive is discharged through the side opening of the adhesive delivery channel and onto the lumen wall. In some embodiments, the distal ends of the adhesive delivery channels 30 of the inner sheath 20 are positioned distal to the distal end of a medical device 10 loaded on the delivery catheter 2.

For deployment of a self-expandable medical device, the outer sheath 16 is retracted to expose the distal end region 21 of the inner sheath 20 so that the adhesive delivery channels 30 extend outwards to discharge adhesive from the side discharge openings onto the lumen wall, and thereafter, the outer and inner sheaths 16, 20 are withdrawn simultaneously to deploy the medical device, and to continue discharging adhesive onto the lumen wall.

For deployment of a balloon expandable medical device, the outer sheath 16 is retracted to expose the distal end region 21 of the inner sheath 20 so that the adhesive delivery channels 30 extend outwards to discharge adhesive from the side discharge openings onto the lumen wall, and thereafter, the outer and inner sheaths 16, 20 are withdrawn simultaneously to expose the medical device and to continue discharging adhesive onto the lumen wall; once the medical device is exposed, the adhesive stops being discharged from the catheter, and the balloon is expanded to deploy the medical device. Thus, the adhesive is applied immediately prior to deployment of the balloon expandable medical device.

Adhesive Delivery Channels Defined by Distal Tip or by Inner Shaft and Distal Tip As discussed above, the adhesive delivery channels 30 can be positioned only in the distal tip 14 (e.g. distal tip includes a catheter adhesive reservoir), or can be positioned in the wall of the inner shaft and in the distal tip (e.g. FIGS. 10-11). Where the adhesive delivery channels are positioned in the wall of the inner shaft, the adhesive delivery channels are positioned between an inner surface and an outer surface of the inner shaft.

Adhesive 60 is discharged from the distal tip 14 onto the lumen wall 70 (FIG. 10) immediately before deployment of the medical device 10 (balloon expandable or self-expandable) (FIG. 11). In some embodiments, the adhesive delivery channels include a nozzle for application of a spray 64 of adhesive 60 onto the lumen wall 70 from the distal tip 14. In one embodiment, the delivery catheter 2 is moved in a first direction as the adhesive 60 is discharged from the distal tip 14 (movement indicated by arrow in FIG. 10), and moved in a second, opposite direction to deploy either a self-expandable or balloon expandable medical device 10 (movement indicated by arrow in FIG. 11). In some embodiments, the discharge openings are oriented at an oblique angle (for example, if the distal tip is tapered as discussed above).

Adhesive Delivery Channels Defined by Distal Tip or by Inner Shaft and Distal Tip, in Combination with Adhesive Delivery Channels Defined by a Sheath or External Element The delivery catheter can include two sets of adhesive delivery channels (not shown). In one aspect a first set of adhesive delivery channels can extend through the distal tip 14 or by the inner shaft 12 and distal tip 14, as discussed above; and a second set of adhesive delivery positioned in the wall of the external element 40, the wall of the outer sheath 20, or the wall of the inner sheath 16.

Adhesive Injection Port/Adhesive Reservoir

An adhesive delivery channel 30 as described above is in fluid communication with, and extending distally from, an adhesive injection port positioned in a proximal region of the catheter, or an adhesive reservoir positioned in a distal region of the catheter. An adhesive fluid path extends from the adhesive injection port or the adhesive reservoir to the discharge opening(s) 32. The adhesive delivery channel in combination with either the adhesive injection port or the adhesive reservoir can be considered to form an adhesive delivery system for the catheter.

Each adhesive delivery channel is in fluid communication with an adhesive injection port. In some embodiments, the adhesive injection port is a proximal opening of an adhesive delivery channel. In one embodiment, the adhesive injection port forms a part of a catheter handle (not shown). In at least one embodiment, the adhesive injection port is in fluid communication with an exterior adhesive reservoir (not shown). In some embodiments the exterior adhesive reservoir is detachable from the adhesive injection port. In one embodiment, the exterior adhesive reservoir is a syringe.

In other embodiments, each adhesive delivery channel is in fluid communication with, and extending distally from, a catheter adhesive reservoir. In this embodiment, an adhesive fluid path extends from the adhesive reservoir to the discharge opening. In one embodiment, the catheter adhesive reservoir is positioned near the distal end region of the delivery catheter (not shown). The catheter adhesive reservoir can be positioned externally, and secured to, to the outer sheath; defined by the outer sheath; defined by the inner shaft; or defined by the distal tip. In some embodiments, an adhesive supply channel is in fluid communication with the external adhesive reservoir and the adhesive injection port for loading of adhesive into the catheter adhesive reservoir. In some embodiments, a microcapsule adhesive is contained in the catheter adhesive reservoir and is pushed into, and out of the adhesive delivery channel with a stylus or a pressure bulb system (not shown).

An adhesive injection port or catheter adhesive reservoir may be in fluid communication with all of the adhesive delivery channels; some of the adhesive delivery channels; or only one of the adhesive delivery channels. Where different adhesives are to be applied, each adhesive can be supplied by a different adhesive injection port or catheter adhesive reservoir with some adhesive delivery channels in fluid communication with one adhesive injection port or catheter adhesive reservoir and other adhesive delivery channels in fluid communication with another adhesive injection port or catheter adhesive reservoir. Thus, for example one adhesive or adhesive component can be applied to the lumen wall and another adhesive or adhesive component can be applied to the medical device.

Mixing Mechanism

In addition, the adhesive delivery system can include a mixing mechanism (not shown). The mixing mechanism is used to mix a two-part adhesive. The mixing mechanism can be positioned at the adhesive injection port, so that the two part adhesive is mixed before the adhesive is ejected into the adhesive delivery channels. Alternatively the mixing mechanism can be positioned at the discharge opening 32 of the adhesive delivery channel 30 so that the two part adhesive is mixed as the adhesive is being discharged from the adhesive delivery channel 30. Thus, the adhesive cure chemistry is delayed until the adhesive exits the adhesive delivery channel 30. When the mixing mechanism is positioned at the discharge opening 32 of the adhesive delivery channel, there are separate streams for each part of the two part adhesive. Thus for example, each adhesive delivery channel is subdivided into two sub-channels with one sub-channel delivering Part A of the two part adhesive and the other sub-channel delivering Part B of the two part adhesive to the mixing mechanism at the discharge opening of the adhesive delivery channel.

Additional Aspects of the Delivery Catheter

In at least one embodiment, the distal tip 14 is tapered from a proximal end to a distal end (e.g. FIGS. 1 and 6). In some embodiments, the distal end of the outer sheath 16 abuts the proximal end of the distal tip 14 and the distal tip 14 is positioned distal to a stent 10 compressed by the outer sheath 16. In other embodiments, the distal tip 14 is positioned distal to a balloon upon which a stent is crimped for delivery. In at least one embodiment, the distal tip 14 is secured to the inner shaft 12. In some embodiments, the distal tip defines a tip lumen in communication with the inner shaft lumen. In one embodiment, the inner shaft lumen and the tip lumen is a guidewire lumen for a guidewire (not shown).

The delivery catheter 2 can be configured to deliver a balloon expandable medical device or a self-expandable medical device. Where the catheter 2 includes a distal tip 14, the medical device is positioned proximal to the distal tip.

When the catheter 2 is configured to deliver a balloon expandable medical device, the catheter includes a balloon positioned in the distal end region of the catheter (not shown). For delivery a medical device is crimped onto a balloon and a sheath, e.g. an outer sheath 16, is positioned around the crimped medical device. For deployment of the balloon expandable medical device, the sheath is withdrawn from the medical device; the balloon expanded to deploy the medical device; and the adhesive is discharged immediately prior to deployment of the medical device. If adhesive is deposited onto the balloon when the balloon deploys the medical device, the outer sheath can be advanced over the balloon for withdrawal of the catheter.

When the catheter 2 is configured to deliver a self-expandable medical device, the catheter 2 can have several loaded delivery configurations.

In one embodiment of a loaded delivery catheter, the outer sheath 16, the compressed self-expandable medical device 10, and the inner shaft 12 are coaxially arranged about the longitudinal axis of the delivery catheter 2, with the inner shaft 12 positioned inside the medical device 10, and the medical device 10 positioned inside the outer sheath 16 (e.g. FIGS. 2-3, for simplicity the inner shaft is not shown). The medical device is deployed upon retraction of the outer sheath 16.

In another embodiment of a loaded delivery catheter, the outer sheath 16, the inner sheath 20, the compressed self-expandable medical device 10, and the inner shaft 12 are coaxially arranged about the longitudinal axis of the delivery catheter 2, with the inner shaft 12 positioned inside the medical device 10, the medical device 10 positioned inside the inner sheath 20, and the inner sheath 20 positioned inside the outer sheath 16 (e.g. FIG. 14, for simplicity the medical device is not shown). The medical device is deployed upon retraction of the sheath 16, 20.

In yet another embodiment of a loaded delivery catheter, the external element 40, the outer sheath 16, the self-expandable medical device 10, and the inner shaft 12 are coaxially arranged about the longitudinal axis of the delivery catheter 2, with inner shaft 12 positioned inside the medical device 10, the medical device 10 positioned inside the outer sheath 16, the medical device 10 being in a compressed delivery state, and the outer sheath 16 positioned inside the external element 40 (e.g. FIGS. 8-9). The medical device is deployed upon retraction of the outer sheath 16.

Figure 5:
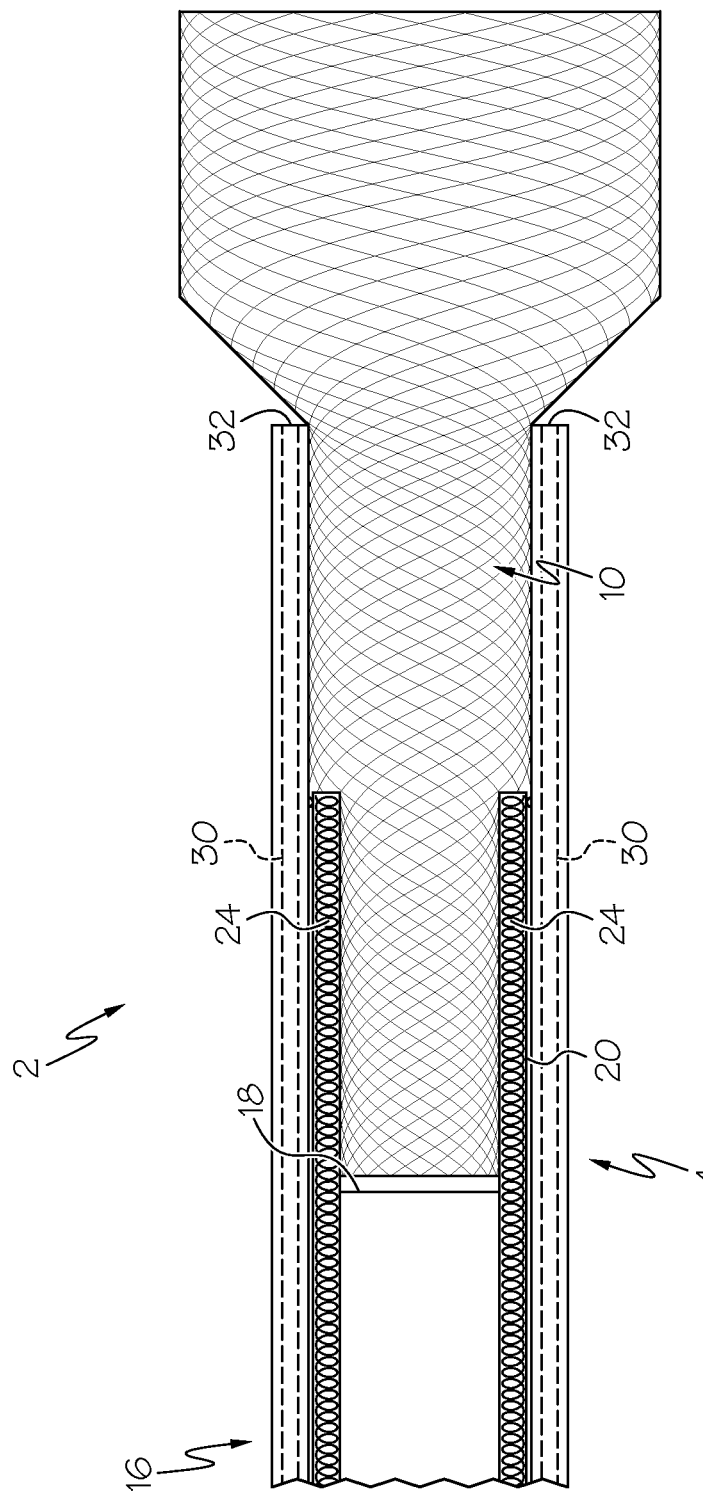
FIG. 5 is a simplified longitudinal cross-sectional view of a sheath retraction system for the delivery catheter of FIG. 1.

As discussed above, in some embodiments, the inner sheath 20 at least partially overlays a medical device 10 compressed in the delivery catheter 2 (e.g. FIG. 5). The inner sheath can be retracted longitudinally, helically, or both helically and longitudinally. In some embodiments, the inner sheath 20 has a constant outer diameter.

In at least one embodiment, the outer sheath 16 is retracted proximally to deploy the medical device 10 (e.g. FIGS. 4-8 and 11-12). In some embodiments, the outer sheath 16 is only longitudinally retractable. In other embodiments, the outer sheath 16 is longitudinally and helically retractable.

In at least one embodiment, the outer sheath 16 is retracted with an outer sheath retraction system that comprises a boss 22 that fits into a track 24. As used in this disclosure, a "boss" is a protrusion. The outer sheath 16 comprises a boss 22 that extends from an inner surface of the outer sheath 16. In some embodiments, the outer sheath 16 has one boss (a single boss). In other embodiments, the outer sheath 16 has a plurality of bosses. Each boss 22 fits into a track 24. The boss 22 travels proximally along the tract 24 to withdraw the outer sheath 16 from the medical device 10. Thus the length of the track is sufficient to withdraw the outer sheath 16 from the compressed medical device 10 for deployment of the medical device. The track 24 can extend longitudinally, helically, or have a portion that extends helically and a portion that extends longitudinally. In some embodiments, the track 24 is defined by an inner stopper 18 (e.g. FIG. 4). In other embodiments, the track 24 is defined by an inner sheath 20 (e.g. FIG. 5).

Figure 4:
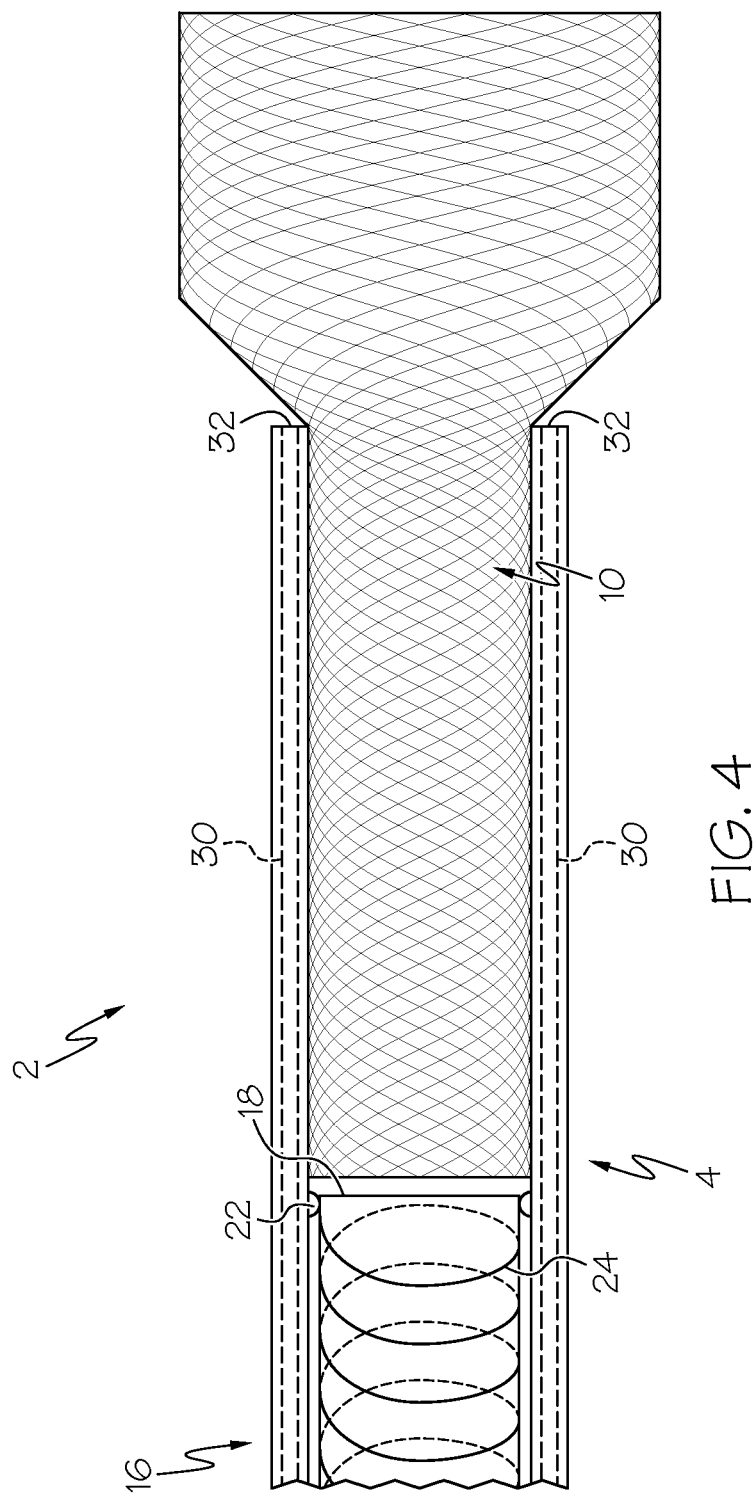
FIG. 4 is a simplified longitudinal cross-sectional view of a sheath retraction system for the delivery catheter of FIG. 1.

In at least one embodiment, the inner stopper 18 is longitudinally adjacent to the proximal end of a medical device 10 loaded onto the delivery catheter 2 (e.g. FIG. 4). In some embodiments, the distal end of the inner stopper 18 abuts the proximal end of the medical device 10. Thus, the distal end of the inner stopper 18 is proximal to the distal end of the outer sheath 16. In one embodiment, the inner stopper 18 prevents the medical device from moving in a proximal direction as the sheath is retracted. The outer surface of the inner stopper 18 defines the track 24. In some embodiments, the inner stopper 18 is secured to the inner shaft 12. In this embodiment, the inner stopper 18 is stationary during the retraction of the outer sheath 16.

In some embodiments, the inner surface of the inner sheath 20 defines the tract 24. In some embodiments, the distal end of the inner sheath 20 is proximal to the distal end of the outer sheath 16. In at least one embodiment, a worm gear, or other suitable mechanism, is positioned towards the proximal end of the delivery catheter 2, and retracts the inner sheath 20 and the outer sheath 16 such that the outer sheath 16 is retracted at a faster rate than the inner sheath 20 so that the ends of the two sheaths 16, 20 are coextensive when the deployment of the medical device 10 has been completed (not shown).

In at least one embodiment, the inner sheath 20 at least partially overlays a medical device 10 compressed in the delivery catheter 2 (e.g. FIG. 5). The inner sheath can be retracted longitudinally, helically, or both helically and longitudinally. A sheath retraction comprising a boss that fits into a tract as discussed above can be used to retract the inner sheath 20. In some embodiments, the inner sheath 20 has a constant outer diameter.

In some embodiments the medical device 10, the delivery catheter 2, or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the medical device 10 is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof Where the therapeutic agent includes a polymer agent, the polymer agent may be a polystyrene-polyisobutylene-polystyrene triblock copolymer (SIBS), polyethylene oxide, silicone rubber and/or any other suitable substrate.

In addition to any materials discussed above, any suitable material (metallic, polymeric, and combinations thereof) can be used to form the parts of the catheter.

In some embodiments, the inner surface of the sheath 16, 20 that overlays the medical device has a lubricious coating for easier movement of the sheath relative to the medical device.

Additional Aspects of Reactive Polyfunctional Oligomers

Examples include a formulation of two types of branched biocompatible molecules (Type A and Type B). Reaction chemistry is second order nucleophilic substitution ($S_N2$) such as thiols and vinyl groups (Michelson addition), or N-hydroxysuccinimide+amines. When the Type A solution is mixed with the Type B solution, reaction ensues.

An example of a Type A molecule is a branched molecule containing multiple N-hydroxysuccinimide groups. The Type A molecules are formulated in a biocompatible aqueous buffer that optimizes use life and reaction speed which is controlled by selection of a specific pH and buffer strength.

An example of a Type B molecule is a branched biocompatible molecule having multiple primary amine end groups. The type B molecule is formulated in a pH controlled buffer solution.

U.S. Pat. No. 6,566,406, incorporated by reference in its entirety, provides exemplifications of this chemistry.

Additional Aspects of a Biocompatible polymer Dissolved in a Water Miscible Solvent The biocompatible polymer is insoluble in water. When the polymer solution in the miscible solvent is delivered into the biological region, aqueous biological fluid will mix with the polymer solution causing the polymer to precipitate.

Additional Aspects of a Free Radical Redox System

This system is similar to the system discussed in Example 1 except it uses a free radical redox system instead of a $S_N2$ reaction mechanism. An example would be branched PEG's with acrylate end groups with are mixed at the appropriate time with Fenton's reagent (a solution of hydrogen peroxide and an iron catalyst). Generation of free radicals with the Fenton's reagent initiates crosslinking of the branched biocompatible molecules. U.S. Pat. No. 6,818,018, incorporated by reference in its entirety, provides examples of this chemistry among others.

Additional Aspects of Adhesives in Microcapsular Bead Form

Adhesives can be delivered in a microcapsular bead form. The bead containing the adhesive can degrade in a short period of time thereby releasing the adhesive; can open based on a chemical reaction with the biological environment; or can be crushed open by the radial expanding force of the medical device. In some embodiments, the microcapsules have adhesive on an outer surface thereof. For example, mucoadhesive microcapsules containing similar or an additional type of adhesive on an outer surface thereof will stick to the lumen wall at or near the ejection location along the medical device, thereby helping to space out and spread the adhesive.

Additional Aspects of Tissue-Adhesive Functional Groups

As discussed in greater detail in commonly assigned US Patent Application No. 2012/0245663, suitable tissue-adhesive functional groups include any functional group that is capable of reacting with the amine groups, thiol groups, and/or other nucleophilic groups present in the proteinaceous tissue surface so as to form covalent bonds between the tissue-adhesive functional groups and the body tissue at the implantation site. In at least one embodiment, tissue-adhesive functional groups are deposited onto the outer surface of the medical device.

Additional Aspects of the Medical Device

As discussed above, the medical device 10 may be a stent or a valve. The stents and valves may be made from any suitable biocompatible materials including one or more polymers, one or more metals or combinations of polymer(s) and metal(s). In some embodiments, the stent has flared ends (e.g. end regions of the stent have a greater diameter than a middle portion of the stent).

In at least one embodiment, the medical device is primed. Priming can include a surface energy increase that might be obtained by a suitable gas plasma treatment. Priming can also include a surface topography change such as an increase in surface topography which might improve adhesion via a mechanical interlocking mechanism.

Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stents and valves may be made of materials with shape memory effect, such as Nitinol; may be made of materials with superelastic properties, such as Nitinol; or may be made of materials which are plastically deformable. In the case of materials with shape memory effect, the stents may be provided with a memorized shape and then deformed to a reduced diameter shape. The stent and valve may restore itself to its memorized shape upon being heated to a transition temperature and having any restraints removed therefrom.

The stents and valves may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the stents disclosed herein.

In some embodiments, the valves include leaflets, as are known in the art. In other embodiments, the valves are ball valves, as are known in the art.

Aspects of the Present Disclosure

Aspects of the delivery catheter discussed above and as presented in the claims, may be combined in any fashion and combination and be within the scope of a delivery catheter of the present disclosure, as indicated by the following aspects:

Aspect 1. A method of implanting a medical device in a body lumen comprising:

advancing a delivery catheter carrying the medical device, the medical device being selected from the group consisting of stents and valves;

discharging an adhesive from the delivery catheter during or immediately before deployment of the medical device, the adhesive being discharged onto the medical device, a wall of the body lumen, or combinations thereof.

Aspect 2. The method of aspect 1, the delivery catheter comprising an adhesive delivery channel having a discharge opening for discharging the adhesive.

Aspect 3. The method of aspect 2, the adhesive delivery channel being a plurality of adhesive delivery channels.

Aspect 4. The method of any one of aspects 2-3, the discharge opening being selected from the group consisting of side discharge openings, distal discharge openings, and combinations thereof.

Aspect 5. The method of aspect 4, the distal discharge openings either facing distally or facing outward relative to the longitudinal axis of the catheter.

Aspect 6. The method of any one of aspects 1-5, wherein discharging the adhesive comprises depositing lines of adhesive.

Aspect 7. The method of any one of aspects 1-5, wherein discharging the adhesive comprise spraying the adhesive.

Aspect 8. The method of any one of aspects 1-5 and 7, the adhesive delivery channel comprising a nozzle for spraying the adhesive.

Aspect 9. The method of aspect 8, the nozzle being a reduced diameter portion of an adhesive delivery channel.

Aspect 10. The method of aspect 9, the reduced diameter portion of the adhesive delivery channel being the discharge opening of the adhesive delivery channel.

Aspect 11. The method of any one of aspects 1-10, wherein the adhesive is discharged onto the medical device.

Aspect 12. The method of aspect 11, wherein only a portion of the medical device has adhesive discharged thereon.

Aspect 13. The method of any one of aspects 1-12, wherein the adhesive is discharged onto the wall of the body lumen.

Aspect 14. The method of any one of aspects 1-13, wherein the adhesive is discharged onto the medical device and onto the wall of the body lumen.

Aspect 15. The method of any one of aspects 1-14, the delivery catheter comprising an adhesive injection port positioned at a proximal region of the delivery catheter, the adhesive injection port in fluid communication with the adhesive delivery channel.

Aspect 16. The method of any one of aspects 1-14, the delivery catheter comprising a catheter adhesive reservoir in fluid communication with the adhesive delivery channel.

Aspect 17. The method of aspect 16, the catheter adhesive reservoir being positioned in a distal region of the delivery catheter.

Aspect 18. The method of any one of aspects 1-17, the medical device being:
a self-expandable medical device, wherein the adhesive is discharged during deployment of the self-expandable medical device;
a self-expandable medical device, wherein the adhesive is discharged immediately before deployment of the self-expandable medical device; or
a balloon expandable medical device, wherein the adhesive is discharged immediately before deployment of the balloon expandable device.

Aspect 19. The method of any one of aspects 1-18, wherein the adhesive is a two part adhesive, further comprising mixing the two part adhesive.

Aspect 20. The method of aspect 19, wherein the two part adhesive is mixed before the adhesive is ejected into the adhesive delivery channels.

Aspect 21. The method of aspect 19, wherein the two part adhesive is mixed as the adhesive is discharged from the adhesive delivery channels.

Aspect 22. The method of aspect 21, wherein the adhesive delivery channel has two sub-channels to separately deliver part of the two part adhesive to a mixing mechanism positioned at a discharge opening of the adhesive delivery channel.

Aspect 23. The method of any one of aspects 2-22, the delivery catheter comprising a tubular outer sheath overlaying the medical device, the adhesive delivery channel secured to the outer sheath.

Aspect 24. The method of aspect 23, the delivery catheter further comprising a coaxial external element secured to the outer sheath, the adhesive delivery channel positioned in a wall of the external element.

Aspect 25. The method of any one of aspects 23-24, wherein the adhesive delivery channel is positioned between an inner surface and an outer surface of the external element.

Aspect 26. The method of aspect 23, wherein the adhesive delivery channel is a non-coaxial external element secured to the outer sheath.

Aspect 27. The method of aspect 26, the non-coaxial external element being at least one tube.

Aspect 28. The method of any one of aspects 23-27, wherein the outer sheath is only retracted longitudinally, and the adhesive is discharged in a longitudinal line or spray.

Aspect 29. The method of any one of aspects 23-27, wherein the outer sheath is retracted longitudinally and helically, and the adhesive is discharged in a helical line or spray.

Aspect 30. The method of any one of aspects 23-29, wherein the discharge opening is a side discharge opening, the side discharge opening being oriented radially outwards to discharge the adhesive onto the inner surface of the body lumen.

Aspect 31. The method of any one of aspects 23-29, wherein the discharge opening is a distal discharge opening.

Aspect 32. The method of any one of aspects 23-31, the medical device being a self-expandable medical device, wherein the adhesive is discharged during deployment of the self-expandable medical device.

Aspect 33. The method of any one of aspects 23-31, the medical device being a balloon expandable medical device, wherein the adhesive is discharged immediately before deployment of the balloon expandable device.

Aspect 34. The method of any one of aspects 2-22, the delivery catheter comprising a tubular outer sheath positioned over the medical device, and an external element secured to the outer sheath;
wherein retracting the outer sheath from the medical device and discharging the adhesive are concurrent.

Aspect 35. A method of operating a delivery catheter comprising an external element secured to an outer sheath, the method of operation comprising discharging an adhesive from the external element as the outer sheath is retracted.

Aspect 36. The method of any one of aspects 34-35, the external element being non-coaxial with the outer sheath, the external element being the adhesive delivery channel.

Aspect 37. The method of any one of aspects 34-35, the external element being coaxial with the outer sheath, the adhesive delivery channel being defined by a wall of the external element.

Aspect 38. The method of any one of aspects 34-35, wherein the adhesive delivery channel is positioned between an inner surface and an outer surface of the external element.

Aspect 39. The method of any one of aspects 2-22, the delivery catheter comprising a tubular outer sheath positioned over the medical device, the adhesive delivery channel being defined by a wall of the outer sheath;
wherein retracting the outer sheath from the medical device and discharging the adhesive are concurrent.

Aspect 40. A method of operating a delivery catheter comprising discharging an adhesive from an adhesive delivery channel positioned in a wall of the outer sheath of the delivery catheter as the outer sheath is retracted.

Aspect 41. The method of any one of aspects 34-40, wherein the outer sheath is only retracted longitudinally, and the adhesive is discharged in a longitudinal line.

Aspect 42. The method of any one of aspects 34-40, wherein the outer sheath is retracted longitudinally and helically, and the adhesive is discharged in a helical line.

Aspect 43. The method of any one of aspects 34-42, wherein the discharge opening is a side discharge opening, the side discharge opening being oriented radially outwards to discharge the adhesive onto the inner surface of the body lumen.

Aspect 44. The method of any one of aspects 34-43, the medical device being a self-expandable medical device, wherein the adhesive is discharged during deployment of the self-expandable medical device.

Aspect 45. The method of any one of aspects 34-43, the medical device being a balloon expandable medical device, wherein the adhesive is discharged immediately before deployment of the balloon expandable device.

Aspect 46. The method of any one of aspects 34-42, the adhesive delivery channel being a plurality of adhesive delivery channels, wherein the plurality of adhesive delivery channels comprises first adhesive delivery channels having a distal discharge opening and second adhesive delivery channels having a side discharge opening oriented radially outwards, the adhesive being discharged from the plurality of adhesive delivery channels onto the outer surface of the medical device and onto the inner surface of the body lumen.

Aspect 47. The method of aspect 46, the medical device being a self-expandable medical device, wherein the adhesive is discharged during deployment of the self-expandable medical device.

Aspect 48. The method of any one of aspects 2-21, the delivery catheter comprising:
an inner sheath overlaying the medical device, the inner sheath comprising a distal end region and the adhesive delivery channel;
an outer sheath having a distal end and positioned over the inner sheath so that the distal end of the outer sheath is distal to the distal end of the inner sheath;
wherein upon retraction of the outer sheath relative to the inner sheath, the adhesive delivery channel extends outward for discharging adhesive onto the lumen wall during or immediately before deployment of the medical device.

Aspect 49. A method of operating a delivery catheter comprising:
exposing a distal end region of an inner sheath by retracting an outer sheath, the distal end region of the inner sheath configured to expand outwards upon being exposed, a wall of the inner sheath defining an adhesive delivery channel; and
concurrently retracting the outer and inner sheaths and discharging an adhesive from the adhesive delivery channel.

Aspect 50. The method of aspect 48, the medical device being a self-expandable medical device, wherein the adhesive is discharged during deployment of the self-expandable medical device.

Aspect 51. The method of aspect 48, the medical device being a balloon expandable medical device, wherein the adhesive is discharged immediately before deployment of the balloon expandable device.

Aspect 52. The method of any one of aspects 48-51, a circumference of the distal end region being discontinuous.

Aspect 53. The method of any one of aspects 48-52, the distal end region formed only by the adhesive delivery channel.

Aspect 54. The method of any of one of aspects 48-53, the adhesive delivery channel being a plurality of adhesive delivery channels separated one from another.

Aspect 55. The method of any of one of aspects 48-54, the adhesive delivery channel being a plurality of adhesive delivery channels and extenders, the adhesive delivery channel and extenders being separated from one another.

Aspect 56. The method of any one of aspects 48-55, the inner sheath being retracted longitudinally.

Aspect 57. The method of any one of aspects 48-55, the inner sheath being retracted helically.

Aspect 58. The method of any one of aspects 48-57, the adhesive delivery channels comprising a shape memory polymer or an electroactive polymer.

Aspect 59. The method of any one of aspects 48-58, the inner sheath further comprising a lubricant coating on an inner surface.

Aspect 60. The method of any one of aspects 48-59 the outer sheath and the inner sheath each comprising a protuberance configured to contact one another after partial retraction of the outer sheath, wherein further retraction of the retracts the inner sheath.

Aspect 61. The method of aspect 60, each protuberance being an annular ring.

Aspect 62. A delivery catheter for a medical device comprising:
an inner shaft;
an inner sheath extending around the inner shaft, the inner sheath comprising a distal end region and an adhesive delivery channel comprising a discharge opening, the adhesive delivery channel forming the distal end region of the inner sheath; and an outer sheath;
wherein the distal end region of the inner sheath is configured to extend outward relative to the inner shaft upon removal of the outer sheath.

Aspect 63. The delivery catheter of aspect 62, wherein the adhesive delivery channel is positioned between an inner surface and an outer surface of the inner sheath.

Aspect 64. The delivery catheter of any one of aspects 62-63, the adhesive delivery channel comprising a nozzle for spraying an adhesive from the adhesive delivery channel.

Aspect 65. The delivery catheter of aspect 64, the nozzle being a reduced diameter portion of the adhesive delivery channel.

Aspect 66. The delivery catheter of aspect 65, the reduced diameter portion being the discharge opening.

Aspect 67. The delivery catheter of aspects 62-66, the discharge opening being selected from the group consisting of side discharge openings, distal discharge openings, and combinations thereof.

Aspect 68. The delivery catheter of aspect 67, the discharge opening being a side discharge opening directed outwards for discharging an adhesive onto a lumen wall.

Aspect 69. The delivery catheter of aspect 67, the discharge opening being a side discharge opening directed inwards for discharging an adhesive onto a medical device during deployment thereof.

Aspect 70. The delivery catheter of aspect 67, the discharge opening being a distal discharge opening for discharging an adhesive onto a lumen wall.

Aspect 71. The delivery catheter of any one of aspects 63-70, the adhesive delivery channel being a plurality of adhesive delivery channels.

Aspect 72. The delivery catheter of any one of aspects 63-71, further comprising a medical device compressed between the inner shaft and the inner sheath.

Aspect 73. The delivery catheter of aspect 72, the medical device being positioned proximal to the distal end region of the inner sheath.

Aspect 74. The delivery catheter of any one of aspects 72-73, the medical device being selected from the group consisting of stents and valves.

Aspect 75. The delivery catheter of any one of aspects 62-74, the inner sheath further comprising a lubricant coating on an inner surface.

Aspect 76. The delivery catheter of any one of aspects 62-75, the outer sheath and the inner sheath each comprising a protuberance configured to contact one another after partial retraction of the outer sheath, the protuberance of the inner sheath being positioned proximal to the protuberance of the outer sheath.

Aspect 77. The delivery catheter of aspect 76, each protuberance being an annular ring.

Aspect 78. The delivery catheter of any one of aspects 62-77, the medical device being a self-expandable medical device, wherein the adhesive is discharged during deployment of the self-expandable medical device.

Aspect 79. The delivery catheter of any one of aspects 62-68 and 70-77, the medical device being a balloon expandable device, wherein the adhesive is discharged immediately before deployment of the balloon expandable medical device.

Aspect 80. A method of implanting a medical device in a body lumen comprising:
advancing a delivery catheter carrying the medical device, the delivery catheter comprising a distal tip;
discharging an adhesive from the distal tip of the delivery catheter onto an inner surface of the body lumen; and
deploying the medical device in the body lumen immediately after discharging the adhesive.

Aspect 81. A method of operating a delivery catheter comprising:
discharging an adhesive from an adhesive delivery channel as the delivery catheter is being retracted, wherein the adhesive delivery channel is positioned in a wall of an inner shaft and in a distal tip secured to the inner shaft.

Aspect 82. The method of aspect 80, wherein the medical device is selected from the group consisting of self-expandable medical devices and balloon expandable medical devices.

Aspect 83. The method of any one of aspects 80-82, the delivery catheter further comprising an adhesive delivery channel having a discharge opening, the adhesive delivery channel positioned in the distal tip.

Aspect 84. The method of aspect 83, the distal tip further comprising a catheter adhesive reservoir in fluid communication with the adhesive delivery channel.

Aspect 85. The method of any one of aspects 80-83, the delivery catheter further comprising an inner shaft secured to the distal tip, the adhesive delivery channel further positioned in a wall of the inner shaft.

Aspect 86. The method of aspect 85, the delivery catheter further comprising an adhesive injection port in fluid communication with the adhesive delivery channel.

Aspect 87. The method of any one of aspects 83-86, the adhesive delivery channel further comprising a nozzle.

Aspect 88. The method of aspect 87, the nozzle being a reduced diameter portion of the adhesive delivery channel.

Aspect 89. The method of aspect 88 the reduced diameter portion being the discharge opening.

Aspect 90. The method of any one of aspects 83-89, the adhesive delivery channel being a plurality of adhesive delivery channels.

Aspect 91. The method of any of one of aspects 80-90, wherein the delivery catheter is moved in a first direction while discharging the adhesive and the delivery catheter is moved in a second direction opposite the first direction while deploying the medical device.

Aspect 92. The method of any one of aspects 80, 82-91, the medical device being self-expandable.

Aspect 93. The method of aspect 92, the self-expandable medical device being positioned between an inner shaft and a sheath as the delivery catheter is advancing.

Aspect 94. The method of aspect 93, the sheath having a distal end abutting a proximal end of the distal tip as the delivery catheter is advancing.

Aspect 95. The method of claims 80, 82-94, wherein deploying the medical device comprises retracting the sheath.

Aspect 96. The method of any one of aspects 80, 82-91, the medical device being balloon expandable, the delivery catheter further comprising a balloon, the medical device being compressed onto the balloon, wherein deploying the medical device comprises expanding the balloon.

Aspect 97. The method of aspect 96, wherein expanding the balloon comprises inflating the balloon with inflation media.

Aspect 98. The method of any one of aspects 80, 82-97, the medical device being selected from the group consisting of stents and valves.

Aspect 99. The method of any one of aspects 80-98, the distal tip being tapered.

Aspect 100. The method of any one of aspects 80-99, the distal tip defining a guidewire lumen.

Aspect 101. A method of operating a delivery catheter comprising:
discharging an adhesive from an adhesive delivery channel as the outer sheath is being retracted.

Aspect 102. The method of aspect 101, wherein a coaxial external element defines the adhesive delivery channel, the coaxial external element secured to the outer sheath.

Aspect 103. The method of aspect 101, wherein a wall of the outer sheath defines the adhesive delivery channel.

Aspect 104. The method of aspect 101, wherein a wall of the inner sheath defines the adhesive delivery channel.

Aspect 105. The method of any one of aspects 101-104, wherein the adhesive delivery channel has either a distal discharge opening or a side discharge opening.

Aspect 106. The method of any one of aspects 101-105, wherein discharging the adhesive comprises spraying the adhesive from the adhesive delivery channel.

Aspect 107. The method of any one of aspects 101-106, further comprising mixing a two-part adhesive prior to ejecting the two-part adhesive into the adhesive delivery channel.

Aspect 108. The method of any one of aspects 101-106, further comprising mixing a two-part adhesive as the adhesive is being discharged from the adhesive delivery channel.

Aspect 109. The method of aspect 108, the adhesive delivery channel having two sub-channels to separately deliver the two-part adhesive to a mixing mechanism positioned at the discharge opening of the adhesive delivery channel.

Aspect 1010. The method of any one of aspects 101 and 104-109, the adhesive delivery channel being a plurality of adhesive delivery channels, wherein a distal end region of each adhesive delivery channel is configured to expand outward upon an initial retraction of the outer sheath from the inner sheath Aspect 1011. A delivery catheter for a medical device comprising an adhesive delivery channel.

Aspect 1012. The delivery catheter of aspect 1011, the delivery catheter further comprising an outer sheath, the adhesive delivery channel being external to the outer sheath.

Aspect 1013. The delivery catheter of aspect 1012, the adhesive delivery channel secured to an outer surface of the outer sheath.

Aspect 1014. The delivery catheter of aspect 1012, the delivery catheter further comprising an external element secured to the outer sheath, the adhesive delivery channel positioned in a wall of the external element.

Aspect 1015. The delivery catheter of aspect 1011, the delivery catheter further comprising an outer sheath, the adhesive delivery channel positioned in a wall of the outer sheath.

Aspect 1016. The delivery catheter of aspect 1011, the delivery catheter further comprising an inner sheath, the adhesive delivery channel positioned in a wall of the inner sheath.

Aspect 1017. The delivery catheter of aspect 1011, the delivery catheter further comprising a distal tip, the adhesive delivery channel positioned in the distal tip.

Aspect 1018. The delivery catheter of aspect 1017, the delivery catheter further comprising an inner shaft, the adhesive delivery channel also positioned in a wall of the inner shaft.

Aspect 1019. The delivery catheter of any one of aspects 1011-1015, the delivery catheter further comprising an inner shaft.

Aspect 1020. The delivery catheter of aspect 1019, the delivery catheter further comprising a distal tip secured to the inner shaft.

Aspect 1021. The delivery catheter of any one of aspects 1019-1020, the delivery catheter further comprising an inner sheath, the inner sheath positioned in a lumen of the outer sheath.

Aspect 1022. The delivery catheter of aspect 1016, the delivery catheter further comprising an inner shaft, the inner shaft positioned in a lumen of the inner sheath.

Aspect 1023. The delivery catheter of aspect 1022, the delivery catheter further comprising a distal tip secured to the inner shaft.

Aspect 1024. The delivery catheter of any one of aspects 1022-1023, the delivery catheter further comprising an outer sheath, the inner sheath positioned in a lumen of the outer sheath.

The above disclosure is intended to be illustrative and not exhaustive.

This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the disclosure such that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A method of implanting a medical device in a body lumen comprising:
    advancing a delivery catheter having the medical device disposed within an interior of the delivery catheter, through the body lumen to a deployment site, the medical device being selected from the group consisting of stents and valves, the delivery catheter defining at least one adhesive delivery channel having at least one discharge opening that either faces distally and extends through a distal end face of the delivery catheter to discharge adhesive in a distal direction distally beyond the distal end face, or that extends through a sidewall of the delivery channel and faces radially outward from the delivery channel relative to a longitudinal axis of the delivery catheter to discharge adhesive in a radially outward direction, for discharging the adhesive therefrom; and
    thereafter, deploying the medical device from the delivery catheter at the deployment site while discharging an adhesive from the adhesive delivery channel in the delivery catheter during deployment of the medical device, the adhesive being discharged onto the medical device, a wall of the body lumen, or combinations thereof.

2. The method of claim 1, the adhesive delivery channel having a plurality of discharge openings for discharging the adhesive.

3. The method of claim 1, the adhesive delivery channel being a plurality of adhesive delivery channels.

4. The method of claim 3, wherein discharging the adhesive comprises depositing a plurality of lines of the adhesive from the plurality of adhesive delivery channels.

5. The method of claim 3, the delivery catheter comprising an outer sheath overlaying the medical device, the adhesive delivery channel secured to the outer sheath.

6. The method of claim 3, the delivery catheter comprising an outer sheath positioned over the medical device, the outer sheath defining the adhesive delivery channel;
    wherein retracting the outer sheath from the medical device and discharging the adhesive are concurrent.

7. The method of claim 3, the delivery catheter comprising:
    an inner sheath overlaying the medical device, the inner sheath comprising a distal end region and the plurality of adhesive delivery channels;
    an outer sheath having a distal end and positioned over the inner sheath so that the distal end of the outer sheath is distal to the distal end region of the inner sheath;
    wherein upon retraction of the outer sheath relative to the inner sheath, the plurality of adhesive delivery channels extend outward for discharging adhesive onto the wall of the body lumen during deployment of the medical device.

8. The method of claim 7, a circumference of the distal end region of the inner sheath being discontinuous.

9. The method of claim 7, the plurality of adhesive delivery channels comprising a shape memory polymer or an electroactive polymer.

10. The method of claim 1, wherein discharging the adhesive comprises spraying the adhesive.

11. The method of claim 10, the adhesive delivery channel comprising a nozzle for spraying the adhesive.

12. The method of claim 1, wherein the adhesive is discharged onto the medical device as the medical device is delivered from the distal end of the delivery catheter.

13. The method of claim 1, wherein the adhesive is discharged onto the wall of the body lumen.

14. The method of claim 1, the delivery catheter comprising an adhesive injection port positioned at a proximal region of the delivery catheter, the adhesive injection port in fluid communication with the adhesive delivery channel.

15. The method of claim 1, the delivery catheter comprising a catheter adhesive reservoir in fluid communication with the adhesive delivery channel.

16. A delivery catheter for a medical device comprising:
an inner shaft;
an inner sheath having a longitudinal axis and extending around the inner shaft, the inner sheath comprising a distal end region and defining at least one adhesive delivery channel comprising a discharge opening, the adhesive delivery channel forming the distal end region of the inner sheath; and
an outer sheath;
wherein the distal end region of the inner sheath is configured to move between a first configuration in which the at least one adhesive delivery channel extends along the longitudinal axis when the inner sheath is disposed within the outer sheath, to a second configuration in which the at least one adhesive delivery channel is moved radially outward relative to the inner shaft upon an initial retraction of the outer sheath.

17. A method of implanting a medical device in a body lumen comprising:
advancing a delivery catheter having the medical device disposed within an interior of the delivery catheter, through the body lumen to a deployment site, the delivery catheter comprising a distal tip, the delivery catheter defining an adhesive delivery channel having a discharge opening positioned in the distal tip;
thereafter, discharging an adhesive from the distal tip of the delivery catheter onto an inner surface of the body lumen at the deployment site; and
deploying the medical device from the delivery catheter in the body lumen at the deployment site immediately after discharging the adhesive.

18. The method of claim 17, the delivery catheter further comprising an inner shaft secured to the distal tip, the adhesive delivery channel further positioned in a wall of the inner shaft.

19. The method of claim 17, wherein the delivery catheter is moved in a first direction while discharging the adhesive and the delivery catheter is moved in a second direction opposite the first direction while deploying the medical device.

20. The method of claim 17, wherein the distal tip of the delivery catheter comprises an adhesive reservoir.

* * * * *